United States Patent [19]

Wang et al.

[11] 4,342,659
[45] Aug. 3, 1982

[54] VIDEO DISC LUBRICANTS

[75] Inventors: Chih C. Wang, Hightstown; Lincoln Ekstrom, Princeton; Thomas C. Lausman, Cranbury, all of N.J.; Henry Wielicki, Wyndmoor, Pa.

[73] Assignee: RCA Corporation, New York, N.Y.

[21] Appl. No.: 65,064

[22] Filed: Aug. 9, 1979

Related U.S. Application Data

[62] Division of Ser. No. 937,819, Aug. 29, 1978, abandoned.

[51] Int. Cl.$^3$ ................................................ C07F 7/08
[52] U.S. Cl. .................................... 252/49.6; 556/456
[58] Field of Search ................. 260/448.2 R; 556/456; 252/49.6

[56] References Cited

U.S. PATENT DOCUMENTS 3,418,353 12/1968 Brown ................................. 556/456
3,833,408 9/1974 Matthies ............................. 117/217
4,159,276 6/1979 Desai et al. ........................ 556/456

Primary Examiner—Paul F. Shaver
Attorney, Agent, or Firm—Birgit E. Morris; R. Hain Swope

[57] ABSTRACT

Molecular distillation of methyl alkyl siloxanes of the formula

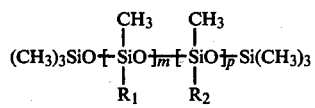

wherein $R_1$ and $R_2$ are alkyl groups of 4-20 carbon atoms and m and p are integers to produce a distillate having a molecular weight fraction wherein the sum of m and p is about 4, produces an improved lubricant for the video disc, a lubricant that is stable to long term storage and to wide variations in temperature and relative humidity.

8 Claims, 3 Drawing Figures

VIDEO DISC LUBRICANTS

This is a division of application Ser. No. 937,819, filed Aug. 29, 1978, now abandoned.

This invention relates to improved lubricants for video discs. More particularly, this invention relates to the purification and fractionation of methyl alkyl siloxane lubricants which give improved performance as video disc lubricants.

BACKGROUND OF THE INVENTION

U.S. Pat. No. 3,833,408, herein incorporated by reference, describes the application of methyl alkyl siloxane compositions as lubricants for conductive video discs comprising a molded plastic disc having audio and video information in the form of geometric variations in a spiral groove. These discs are coated first with a conductive material which acts as a first electrode, then with a dielectric layer and a final layer of lubricant. A metal tipped stylus acts as a second electrode of a capacitor and the information signals are monitored by the stylus which notes changes in capacitance between the stylus and the disc surfaces as the information, in the form of depressions, passes beneath the stylus.

Further developments in this system have produced a video disc which is made of a conductive plastic material, e.g., a PVC copolymer resin containing sufficient amounts of conductive carbon particles so that the disc can provide capacitance readout, while the plastic resin surrounds the carbon particles providing a dielectric surface layer on the conductive particles. This development has eliminated the need for separate coatings of metal and dielectric on the plastic disc.

The stylus, formerly made of metallized sapphire, has also been improved so that metallized diamond can be used. Diamond is a harder, longer wearing material than sapphire, and also requires good lubrication of the disc surface.

Video discs are also being developed which do not require a conductive surface or a grooved surface, the stylus being maintained in synchronization with the information pattern track by means of electrical signals rather than the groove walls.

These changes in the materials used for the video disc and stylus have somewhat changed the requirements for the lubricant and in certain respects the commercially available methyl alkyl siloxane lubricant is now unsatisfactory. One commercially available methyl alkyl siloxane composition has the formula

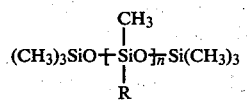

wherein R is a straight chain decyl group, and n is an integer. This material has a molecular weight of about 1500 and a viscosity of about 50 centistokes and is sold by General Electric Company as SF-1147. This composition also contains about 1.5 percent of antioxidant compounds.

When the present video discs molded from carbon-loaded PVC compositions are spray coated with the SF-1147 lubricant and played back with a diamond stylus, the playback performance and stability are less than desirable. Thus an attempt was made to improve the performance of this class of lubricant and the present invention resulted.

SUMMARY OF THE INVENTION

Figure 3:
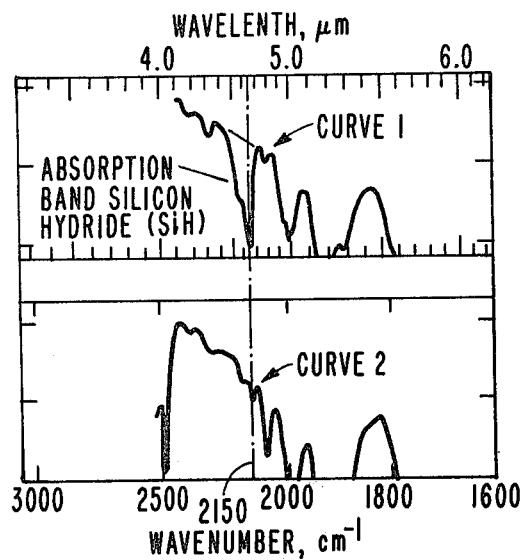
FIG. 3 shows the infrared spectrum of distilled and undistilled methyl alkyl siloxane compositions at 2150 $cm^{-1}$.

We have found that the methyl alkyl siloxanes having the formula

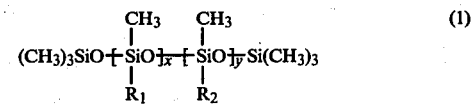

wherein $R_1$ and $R_2$ are alkyl groups of 4–20 carbon atoms, x is an integer of 2–4 and y is an integer of 0–2 and wherein the sum of x and y is 4 or less, have improved lubricity for video disc applications and improved stability to high temperatures, high and low humidity conditions and improved resistance to ageing.

DETAILED DESCRIPTION OF THE INVENTION

The methyl alkyl siloxane compositions of the invention have a distillation temperature of about 100°–205° C. at a pressure of $10^{-5}$ torr, have a molecular weight range of about 500–800 and a polydispersity, defined as the weight average molecular weight divided by the number average molecular weight, of less than about 1.07. The fractions useful herein can be obtained by molecular distillation of a mixed siloxane starting material of the formula

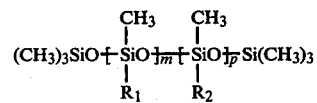

wherein $R_1$ and $R_2$ are as defined above and m and p are integers, under high vacuum low temperature conditions, to obtain a narrow molecular weight fraction.

Molecular distillation is known and is described in "Molecular Distillation of Thermally Supersensitive Liquids", Frank et al, Analytical Chemistry, Vol. 36, No. 11, October 1964. The method can be explained in detail by referring to FIG. 1 which is a schematic view of a molecular still 10. The material to be distilled is fed to feed reservoir 12 which is evacuated by diffusion pump 14 through line 16 which passes through a liquid nitrogen trap 18. The feed reservoir 12 is connected to a distillation chamber 20 containing a glass column 22 which has a spiral glass winding 24 wrapped around it and a receptacle 26 at one end to contain hot fluid. The distillation chamber 20 also contains two additional receptacles, a distilland receptacle 28 and a distillate receptacle 30. A feed tube 32 allows material from the feed reservoir 12 to flow to the distillation chamber 20 through valve 34. A high vacuum is maintained in the distillation chamber 20 through line 36, which also leads to the diffusion pump 14. During operation, the system is evacuated to an initial pressure of about $10^{31}$ 7 torr. Boiling water is maintained in the receptacle 26 and rises through column 22 to heat the said column and the glass winding 24 to a temperature of about 100° C. The control valve 34 is opened to allow a small stream of the material to be distilled to drop onto the heated column 22 from the feed reservoir 12. The material is spread out by the wrapped coil 24 to form a smooth, thin film which is turned over periodically as it passes along the winding 24, enabling the more volatile constituents to evaporate. The material which vaporizes at 100° C. or less evaporates from the heated column 22 and is condensed on the wall of the distillation column 20, flows down the wall and is collected in distillate receptacle 30. The remaining material is collected in distilland receptacle 28. To separate out the materal which boils above 100° and below 205° C., for example, the receptacle 26 is filled with benzyl alcohol, which boils at 205° C., and the distillate from the first fractionation is fed to the feed reservoir 12 and the distillation repeated. The desired distillate collects in distillate receptacle 30 as before and the higher boiling, higher molecular weight fractions are collected in distilland receptacle 28. By using this method of fractionation, the liquid bulk material itself is not heated, but only contacts a heated column where it undergoes a collision-free evaporation at minimum temperatures with the least damage to thermally sensitive molecules.

We have found that molecular distillation of the present methyl alkyl siloxane feedstock not only fractionates the feedstock, but also purifies it, both by removing all antioxidant compounds and chromophores and silicon hydrides as well, thereby providing a much improved lubricant for the video disc. This purification result was highly unexpected and surprising and is highly desirable, since hydrides are chemically active and can produce gel formation which would lead to dropouts and increased noise on playback of the video disc.

The presence of aromatics such as metal-aromatic complex chromophores and antioxidants is also highly undesirable since such compounds are reactive to the video disc surface and contribute to a deterioration of the playback quality with time. The antioxidants generally added to the methyl alkyl siloxane compounds are in the form of both free antioxidants and chemically bound antioxidants. The free antioxidant has the formula

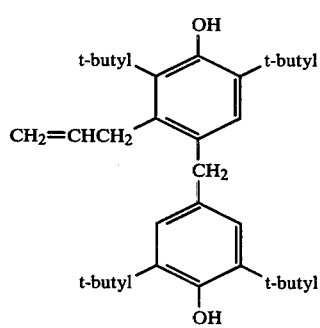

and the chemically bound antioxidant has the formula

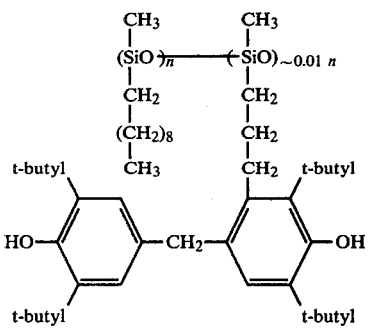

Since the concentration of unbound antioxidant varies from batch to batch, leading to nonuniformities in playback performance of the video disc, the unbound antioxidant can be removed by dissolving in acetone and separating the acetone layer from the methyl alkyl siloxane. However, the presence of the chemically bound antioxidant renders the video disc unplayable, often in a matter of weeks, and thus the presence of aromatic impurities and antioxidant compounds cannot be tolerated at all in the lubricant for the present video discs.

That the present molecular distillation procedure would remove silicon hydrides, particularly to the distilland portion or high molecular weight fraction, was highly unexpected, since silicon hydrides are generally low boiling compounds. It is believed that even at comparatively low temperatures, the hydrides present are reacting with the methyl alkyl siloxane compounds, either to produce higher molecular weight fractions or to produce gelling. This also contributes to the ageing process by using up the lower molecular weight fractions and producing gels which lead to a massive dropout of information during playback of the video disc. This result was highly unexpected.

The fractionated methyl alkyl siloxanes of the invention can be dissolved in a suitable solvent, such as heptane or isopropanol or other solvent which is inert with respect to the disc surface, typically at a loading of from about 0.2 to 2.0 percent by weight of the solution of the methyl alkyl siloxane. The solution is then sprayed onto the disc surface to form a siloxane film about 200–300 angstroms thick. The lubricant film can also be applied by evaporation.

The present lubricant fractions do not age, are stable with respect to atmospheric effects and provide high uniformity and reproducibility for the video disc. In addition, the fractions provide excellent lubricity as measured by low stylus and disc wear, and improved initial playback performance.

The invention will be further illustrated by the following Examples but the invention is not to be limited to the details described therein. In the Examples, percent is by weight unless otherwise noted.

EXAMPLE 1

A methyl alkyl siloxane feedstock having the formula

Figure 1:
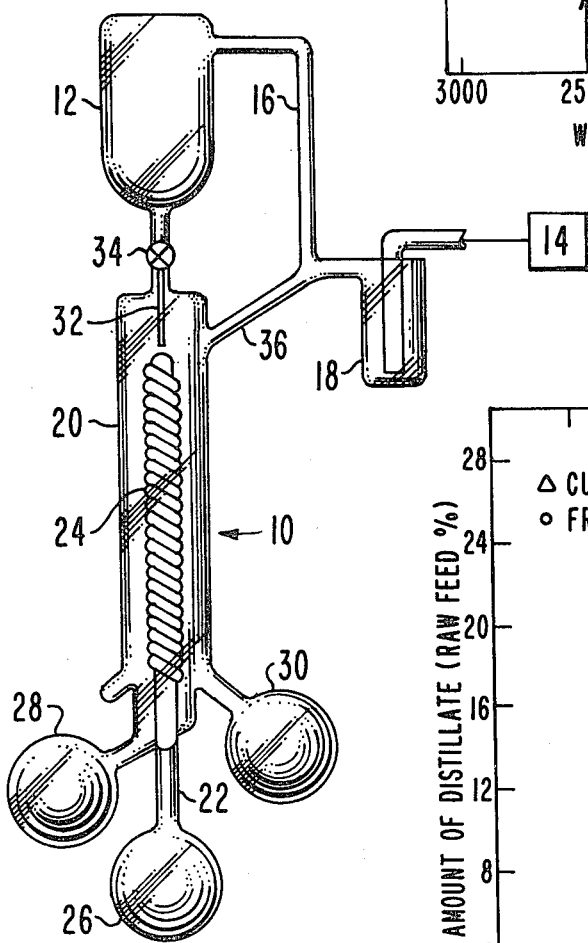
FIG. 1 is a cross-sectional view of a molecular distillation apparatus useful in preparing compositions of the invention.

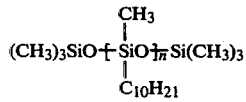

wherein n is an integer from 1 to about 8, having a viscosity of 49.4 centistokes at 22° C., a number average molecular weight of 1239 and a weight average molecular weight of 1557, thus a polydispersity of 1.26, and a refractive index of 1.4463 was molecularly distilled at an average pressure of $10^{-5}$ torr in a distillation apparatus according to FIG. 1.

Figure 2:
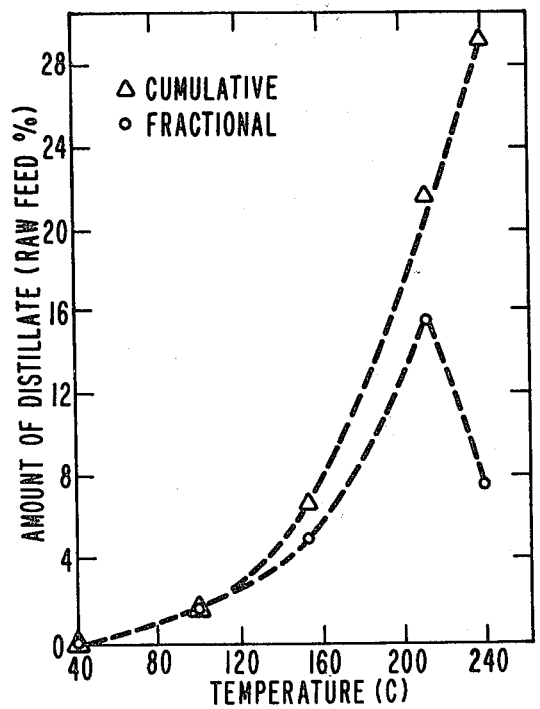
FIG. 2 is a graph which shows the variation in amount of distillate versus temperature.

FIG. 2 shows the amount of distillate as a percent by weight of the feedstock versus temperature.

The fraction which distilled at from 100°–205° C. was collected.

The distillate had a viscosity of about 14 centistokes at 25° C.; a weight average molecular weight of 660, which corresponds to a composition of the general formula (1) wherein y is 0, x is 3 and $R_1$ is decyl, a dispersity of 1.06 and a refractive index of 1.435.

The color of the distillate was measured by determining optical density at various wavelengths for a 1.0 millimeter thick sample and compared to the feedstock color and the distilland color after molecular distillation. The data are summarized below in Table I.

TABLE I

| Sample | Optical Density | | |
|---|---|---|---|
|  | 500 nm | 400 nm | 300 nm |
| Feedstock | 0.060 | 0.125 | 1.60 |
| Distillate 100–205° C. | 0.035 | 0.055 | 1.40 |
| Distilland | 0.080 | 0.17 | 1.80 |

Thus the distillate contains less color-forming material than either the feedstock or the distilland at all wavelengths tested.

The hydride content of the distillate was also greatly reduced from that of the feedstock. As shown by infrared absorption, at a wavelength of 2150 cm$^{-1}$ (SiH) for a 1.0 millimeter thick sample, the feedstock contained about 5–12 cm$^{-1}$ of silicon hydride. The distillate contained less than 0.1 cm$^{-1}$ hydride. The infrared spectra for the feedstock is shown in Curve 1 and the distillate spectra is shown in Curve 2 of FIG. 3.

Thus molecular distillation both fractionates and purifies the methyl alkyl siloxane feedstock.

EXAMPLE 2

The feedstock of Example 1 was molecularly distilled into 5 fractions using appropriate heating fluids and various measurements were taken. The data are summarized in Table II below, wherein fraction I was collected at 40° C., fraction II was collected at 100° C., fraction III was collected at 153° C., fraction IV was collected at 211° C. and fraction V was collected at 239° C.

TABLE II

| Fractions | Density, gm./ml. at 22° C. | Viscosity, cs at 22° C. | $\overline{M_n}$ | $\overline{M_w}$ | Polydispersity | Refractive Index, 22° C. |
|---|---|---|---|---|---|---|
| Feedstock | 0.868 | 49.4 | 1239 | 1557 | 1.26 | 1.4463 |
| Distilland I | 0.868 | 49.2 | 1216 | 1507 | 1.24 | 1.4452 |
| Distilland II | 0.869 | 53.0 | 1323 | 1654 | 1.25 | 1.4453 |
| Distilland III | 0.869 | 55.9 | 1450 | 1794 | 1.24 | 1.4455 |
| Distilland IV | 0.874 | 63.2 | 1525 | 1872 | 1.23 | 1.4472 |
| Distilland V | 0.874 | 73.5 | 2229 | 2700 | 1.21 | — |
| Distillate II | 0.849 | 10.6 | 500 | 526 | 1.05 | 1.4353 |
| Distillate III | 0.852 | 15.5 | 644 | 690 | 1.07 | 1.4363 |
| Distillate IV | 0.862 | 22.7 | 800 | 836 | 1.05 | 1.4385 |
| Distillate V | 0.863 | 27.9 | 1248 | 1304 | 1.04 | — |

The above table shows that methyl alkyl siloxanes can be fractionated into narrow molecular weight fractions by the molecular distillation technique.

EXAMPLE 3

A series of video discs were tested by applying various lubricant compositions and fractions to the disc by evaporation or spraying techniques and playing back with a titanium metallized diamond stylus.

Lubricant A was a methyl decyl siloxane of the formula

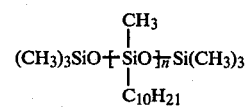

with a molecular weight range as described in Example 1, free of any antioxidant and was applied by vacuum evaporation; lubricant B was the same lubricant applied by spraying from a 1 percent solution in heptane; and lubricant C was the fraction molecularly distilled at 100°–205° C., also applied by spraying as above. The lubricant layers were about 200 angstroms thick.

The quality of the video discs during playback was measured by determining the carrier distress time, which is measured by adding the amount of time, in seconds (but discounting intervals of less than 10 microseconds) during total disc playback when the R.F. output of the player arm is less than 150 millivolts peak to peak, and the time when the R.F. output gave above 8.6 megahertz or below 3.1 megahertz in frequency, indicating a defect. Such defects are noted by the viewer as dropouts. The pass criterion for a video disc is a maximum of 3 seconds in 30 minutes of playback time, and good video quality is considered to be less than 0.3 second in 30 minutes of playback.

Twelve discs having the above lubricants were tested and the percentage of discs which passed each standard was calculated. The data are summarized below in Table III.

TABLE III

| Lubricant | Carrier Distress Time, sec./30 min. | | | |
|---|---|---|---|---|
|  | % ≤ 0.3 sec. | % ≤ 1 sec. | % ≤ 3 sec. | % ≤ 6 sec. |
| A | 41.7 | 58.4 | 83.4 | 100 |
| B | 66.7 | 75 | 91.7 | 91.7 |
| C | 91.7 | 91.7 | 91.7 | 91.7 |

Stylus and disc surface wear tests were made on the above twelve discs by carrying out 35 playbacks on the same 20 minute band of each disc and measuring styli wear and examining the disc surfaces before and after the test for gross, visible wear and significant surface damage visible to the eye and/or under a microscope. The data are summarized below in Table IV.

TABLE IV

| Lubricant | Stylus wear, μ$^3$/hour | % of discs with gross wear and significant surface damage |
|---|---|---|
| A | 0.003 | 25 |
| B | 0.014 | 33.3 |
| C | 0.003 | 8.4 |

EXAMPLE 4

The effect of low humidity on a lubricant fraction as in Example 1, was tested by measuring the carrier distress time of 12 video discs under ambient conditions (76° F. and 18 percent relative humidity, hereinafter RH). All of the discs had carrier distress times of less than 0.3 seconds in 30 minutes of playback. They were then stored at 66° F. and 6 percent RH for 72 hours and played again. All of the discs played well and had a carrier distress of less than 0.3 second in 30 minutes of playback.

When a feedstock lubricant was applied to video discs and tested as above, 42 percent of the discs exhibited carrier distress times of less than 0.3 second and 75 percent of the discs had carrier distress times of less than 3 seconds in 30 minutes of playback. This was unchanged after low humidity storage.

EXAMPLE 5

The effect of low temperature on the present lubricant was tested by measuring carrier distress times of 12 video discs coated with the fractionated lubricant as in Example 1 under ambient conditions (76° F., 20 percent RH). All of the discs had a carrier distress time of less than 0.3 second in 30 minutes of playback. They were then stored in a low temperature chamber at 59°–62° F. and 25 percent RH for 72 hours and immediately played again. All of the discs exhibited good performance before and after storage and all still had a carrier distress time of less than 0.3 seconds in 30 minutes of playback.

When a feedstock lubricant control was applied and tested as above, only 33 percent of the discs had carrier distress time of less than 0.3 second and 75 percent of the discs had carrier distress times of less than 3 seconds in 30 minutes of playback. These results were unchanged after low temperature storage.

EXAMPLE 6

The effect of high temperature and high humidity on the present lubricant was tested by measuring carrier distress time of 12 video discs coated with the fractionated lubricant as in Example 1 after storage in a chamber at 95° F. and 75 percent RH for 24 hours. Carrier distress time results are summarized below in Table V.

TABLE V

| Lubricant | Carrier Distress Time, sec./30 min. | | | |
|---|---|---|---|---|
| | % ≦ 0.3 sec. | % ≦ 1 sec. | % ≦ 3 sec. | % ≦ 6 sec. |
| A | 16.7 | 66.7 | 100 | 100 |
| B | 16.7 | 50 | 83.3 | 100 |
| C | 33.3 | 83.3 | 100 | 100 |

EXAMPLE 7

A mixed methyl alkyl siloxane of the formula

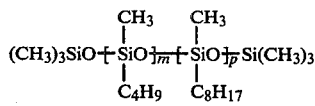

wherein m and p are integers of 2–7 was prepared and molecularly distilled to collect the fraction boiling from 100°–205° C. This lubricant fraction was sprayed from a 1 percent heptane solution onto a video disc as in Example 1. Playback data initially and after storage at high temperature and high humidity conditions (95° F. and 75 percent RH) are summarized below in Table VI.

TABLE VI

| | Carrier Distress Time, sec./30 min. | | | |
|---|---|---|---|---|
| | % ≦ 0.3 sec. | % ≦ 1 sec. | % ≦ 3 sec. | % ≦ 6 sec. |
| Initial play | 87.5 | 100 | 100 | 100 |
| After storage | 12.5 | 62.5 | 62.5 | 87.5 |

EXAMPLE 8

A series of methyl alkyl siloxanes of the formula

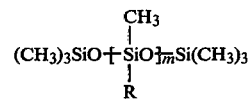

wherein R was hexyl, octyl and dodecyl respectivly and m was an integer of 2–7 were prepared. Each lubricant was sprayed on 8 video discs and the carrier distress time measured. The data are summarized below in Table VII.

TABLE VII

| | Carrier Distress Time, sec./30 min. | | | |
|---|---|---|---|---|
| Initial Play | % ≦ 0.3 sec. | % ≦ 1 sec. | % ≦ 3 sec. | % ≦ 6 sec. |
| C$_6$ Lubricant | 87.5 | 100 | 100 | 100 |
| C$_8$ Lubricant | 87.5 | 87.5 | 100 | 100 |
| C$_{12}$ Lubricant | 87.5 | 100 | 100 | 100 |

The discs were then stored at 95° F. and 75 percent RH for 72 hours and retested. The carrier distress data obtained are summarized below in Table VIII.

TABLE VIII

| | Carrier Distress Time, sec./30 min. | | | |
|---|---|---|---|---|
| After Storage | % ≦ 0.3 sec. | % ≦ 1 sec. | % ≦ 3 sec. | % ≦ 6 sec. |
| C$_6$ Lubricant | 0 | 62.5 | 62.5 | 87.5 |
| C$_8$ Lubricant | 12.5 | 75 | 100 | 100 |
| C$_{12}$ Lubricant | 12.5 | 62.5 | 87.5 | 100 |

Stylus wear tests were also made. All of the tests showed stylus wear below 0.04μ$^3$/per hour.

COMPARATIVE EXAMPLE

A commercially available methyl alkyl siloxane composition sold as SF-1147 was treated to remove free antioxidant as follows: a lubricant was shaken with an equal volume of acetone twice and the layers separated. The free antioxidant is dissolved in the acetone layers along with some low molecular weight silicone oils. The siloxane layer was collected, stripped at 80° C. under vacuum and evacuated at 10 millimeters of mercury at 80° C. to remove all free antioxidant, while leaving the chemically bound antioxidant and the molecular weight distribution of the feedstock intact. This composition was then molecularly distilled as in Example 1 and the fraction distilling between 100°–205° C. was collected.

The lubricant fraction was applied by spray coating from heptane onto a video disc. The initial playback data was good; 84 percent of 12 discs had a carrier distress time of 0.3 second in 30 minutes of playback or less. The discs were then stored for 1 week under ambient conditions. Very high carrier distress times, about 100 seconds up to about 1000 seconds in 30 minutes of playback, were noted on all discs. The lubricant was found to have been removed in places, indicating ageing and lack of compatibility with the present disc system when chemically bound antioxidant is present in the lubricant.

We claim:

1. A lubricant composition for a video disc comprising a methyl alkyl siloxane fraction of the formula

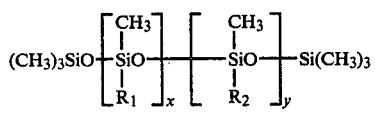

wherein $R_1$ and $R_2$ are alkyl groups of 4–20 carbon atoms, x is an integer of 2–4, y is an integer of 0–2 and wherein the sum of $x+y$ is 4 or less, said fraction having a distillation temperature of about 100°–205° C. at a pressure of $10^{-5}$ torr and wherein said composition is free of antioxidant.

2. The lubricant composition according to claim 1 wherein y is 0 and $R_1$ is decyl.

3. The lubricant composition according to claim 1 wherein y is 0 and $R_1$ is octyl.

4. The lubricant composition according to claim 1 wherein y is 0 and $R_1$ is hexyl.

5. The lubricant composition according to claim 1 wherein y is 0 and $R_1$ is dodecyl.

6. The lubricant composition according to claim 1 wherein $R_1$ is butyl and $R_2$ is octyl.

7. The lubricant composition according to claim 1 wherein $R_1$ and $R_2$ are alkyl of 4–12 carbon atoms.

8. A method of purifying and fractionating a composition of the formula

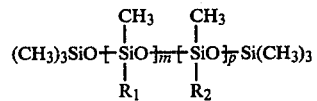

wherein $R_1$ and $R_2$ are alkyl groups of 4–20 carbon atoms and m and p are integers which comprises molecularly distilling said composition and collecting the fraction which distills at from about 100°–205° C.

* * * * *